United States Patent
Wang

(10) Patent No.: US 7,704,946 B2
(45) Date of Patent: Apr. 27, 2010

(54) REVERSIBLE INHIBITION OF PYRAMIDAL GAP JUNCTION ACTIVITY

(75) Inventor: Yun Wang, Chestnut Hill, MA (US)

(73) Assignee: Caritas St. Elizabeth's Medical Center, Boston, MA (US)

( * ) Notice: Subject to any disclaimer, the term of this patent is extended or adjusted under 35 U.S.C. 154(b) by 299 days.

(21) Appl. No.: 11/800,113

(22) Filed: May 3, 2007

(65) Prior Publication Data

US 2008/0058260 A1    Mar. 6, 2008

Related U.S. Application Data

(60) Provisional application No. 60/798,045, filed on May 5, 2006.

(51) Int. Cl.
*A61K 38/17* (2006.01)
*A61K 38/04* (2006.01)

(52) U.S. Cl. ............................................. 514/2; 435/4

(58) Field of Classification Search ........................ None
See application file for complete search history.

(56) References Cited

U.S. PATENT DOCUMENTS 5,652,092 A   7/1997   Vitek et al.
6,787,523 B1 *  9/2004   Schenk ........................ 514/21

OTHER PUBLICATIONS

Lemere CA et al. Amyloid-beta immunization in Alzheimer's disease transgenic mouse models and wildtype mice. Neurochem Res. 2003; 28(7):1017-1027.*
Nakase T & Naus CGC. Gap junctions and neurological disorders of the central nervous system. Biochimica et Biophysica Acta, 2004; 1662:149-158.*
Nemani VM & Binder DK. Emerging role of gap junctions in epilepsy. Histol Histopathol. Jan. 2005; 20(1):253-259.*
Pike CJ et al. Neurodegeneration induced by beta-amyloid peptides in vitro: The role of peptide assembly state. J. Neurosci. 1993; 13(4):1676-1687.*
Romanelli MF et al. Advanced Alzheimer's disease is a risk factor for late-onset seizures. Arch Neurol. 1990; 47(8):847-850.*
Salameh A & Dhein S. Pharmacology of gap junctions. New pharmacological targets for treatment of arrhythmia, seizure and cancer? Biochim Biophys Acta. 2005; 1719:36-58.*
Shemer I et al. Non-fibrillar beta-amyloid abates spike-timing dependent synaptic potentiation at excitatory synapses in layer 2/3 of the neocortex by targeting postsynaptic AMPA receptors. Eur J Neurosci, Apr. 2006; 23(8):2035-2047.*
Freier DB et al. Abeta25-35-induced depression of long-term potentiation in area CA1 in vivo and in vitro is attenuated by verapamil. J Neurophysiol. 2003; 89:3061-3069.*
Gajda Z et al. Involvement of gap junctions in the manifestation and control of the duration of seizures in rats in vivo. Epilepsia, 2003; 44(12):1596-1600.*
Gajda Z et al. Quinine, a blocker of neuronal Cx36 channels, suppresses seizure activity in rat neocortex in vivo. Epilepsia, 2005; 46(10):1581-1591.*
Gigout S et al. Effects in vitro and in vivo of a gap junction blocker on epileptiform activities in a genetic model of absence epilepsy. Epilepsy Res. Apr. 2006; 69:15-29.*
Kamenetz et al., APP processing and synpatic function, Neuron, 27 Mar. 2003, vol. 37, No. 6, pp. 925-937; p. 929, para 2; p. 931, Fig 5E; p. 932, para 3; and p. 934, para 1 [online]. [Retrieved on Sep. 11, 2007].
Steinbach et al., Hypersensitivity to seizures in Beta-amyloid precursor protein deficient mice, Cell Death and Differentiation, Oct. 1998, vol. 5, No. 10, pp. 856-866; p. 858, abstract; p. 859, para 3; and p. 864, para 2 [online]. [Retrieved on Sep. 11, 2007].

* cited by examiner

*Primary Examiner*—Elizabeth C. Kemmerer
*Assistant Examiner*—Kimberly Ballard
(74) *Attorney, Agent, or Firm*—Pierce Atwood LLP; Kevin M. Farrell; David J. Wilson

(57) ABSTRACT

The present invention relates to a novel method of inhibiting gap junction-mediated signaling in pyramid cells. Pyramidal gap junctions are quickly and reversibly inhibited by beta-amyloid or biologically active fragments thereof. The present invention also relates to the use of beta-amyloid as an anticonvulsant for the treatment of epilepsy and other pathological hypersynchrony conditions in humans and non-human animals.

10 Claims, 2 Drawing Sheets

SEQUENCE LISTING

```
<160> NUMBER OF SEQ ID NOS: 3

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Gly Ser Asn Lys Gly Ala Ile Ile Gly Leu Met
 1               5                  10
```

REVERSIBLE INHIBITION OF PYRAMIDAL GAP JUNCTION ACTIVITY

BACKGROUND OF THE INVENTION

Synapses are specialized junctions through which cells of the nervous system signal to one another and to non-neuronal cells such as muscle or gland cells. A cell sending a signal is referred to as a pre-synaptic cell and a cell receiving a signal as a post-synaptic cell. Synapses can be electrical or chemical. Chemical synapses are more common and are much wider, typically 20 to 40 nm.

An electrical synapse is a reciprocal, mechanical, and electrically conductive link between two neurons that forms at a narrow gap between the pre- and post-synaptic cells. Electrical synapses are also called gap junctions. A gap junction is formed by many intercellular protein complexes or junctional channels that directly connect the cytoplasm between adjacent cells. The intercellular protein complex may differ among the gap junctions formed by different types of neurons. Typically, gap junctions are about 3.5 nm across and allow direct transmission of signals (including chemical and electrical signals) between neurons. Through a gap junction, molecules and ions can freely pass between the connected cells. Unlike chemical synapses, electrical synapses do not need receptors to recognize chemical messengers, thus signaling across electrical synapses is faster than that which occurs across chemical synapses. Because of the speed of transmission, electrical synapses occur in escape mechanisms and other processes that require quick responses.

It has been revealed that synchronization of neuronal activity is the most important and primary function of gap junctions in the mammalian central nervous system (Bennett, M. V. & Zukin, R. S., *Neuron* 41, 495-511 (2004); Galarreta, M. & Hestrin, S., *Nat Rev Neurosci* 2, 425-33 (2001); Connors, B. W. & Long, M. A., *Annu Rev Neurosci* 27, 393-418 (2004); Cruikshank, S. J., et al., *Prog Brain Res* 149, 41-57 (2005)). The mammalian neocortex and hippocampus often generate synchronized, rhythmic patterns of activity that vary with behavioral states. Synchronized neuronal activity can exhibit a fast waveform (4-12 Hz for θ frequencies and 20-70 Hz for γ frequencies) or an ultrafast waveform (called "ripple" oscillations in the range of 100-600 Hz).

Pyramidal cells are large, pyramid-shaped excitatory neurons found in the hippocampus and cerebral cortex. Gap junctions between pyramid cells are fundamental to the generation of synchronized activity, especially ultrafast frequency synchronizations (Maier, N. et al., *J Physiol* 541, 521-8 (2002); Hormuzdi, S. G. et al., *Neuron* 31, 487-95 (2001); Buhl, D. L., et al., *J Neurosci* 23, 1013-8 (2003)). These ultrafast synchronizations may play a role in neuronal processing in the hippocampal and neocortical areas, such as sensory perception, motor performance, attention, and memory consolidation (Bennett, M. V. & Zukin, R. S., *Neuron* 41, 495-511 (2004)). Electrophysiological studies have implicated the ultrafast rhythms via pyramidal gap junctions in the generation of pathological hypersynchrony of neuronal activity. Epilepsy seizures are one example of such hypersynchrony (Ponomarenko, A. A., et al., *Usp Fiziol Nauk* 33, 34-42 (2002); Nyikos, L., et al., *Neuroscience* 121, 705-17 (2003); Nemani, V. M. & Binder, D. K., *Histol Histopathol* 20, 253-9 (2005)). Gap junction activity is the synaptic basis for epilepsy seizure.

Gap junction inhibitors have shown powerful anticonvulsant effects, in both in vitro and in vivo studies (Nyikos, L., et al., *Neuroscience* 121, 705-17 (2003)). Known gap junction inhibitors include octanol, heptanol, carbenoxolone, oleamide, halothane, and 18-α and 18-β-glycyrrhetinic acid. Due to the high frequency of side effects, the use of these compounds is limited and they can be unreliable as therapeutics (Yukari Takeda et al., *Am J Physiol Gastrointest Liver Physiol.* 288: G832-G841 (2005); Abrahamsson H, and Dotevall G., *Scand J Gastroenterol Suppl.*, 55:117-20 (1979)). What is needed is a method of inhibiting gap junction activity with fewer side effects.

SUMMARY OF INVENTION

The present invention provides a novel method of inhibiting the activity at pyramidal gap junctions. The method involves quickly inhibiting the activity of these pyramidal gap junctions by administering beta amyloid (Aβ), a peptide which occurs naturally in biological fluids. Aβ may offer safety advantages when compared with existing chemical compounds with undesirable side-effects. The present invention is further based on the finding that the inhibition caused by Aβ is reversible. Experimental results suggest that Aβ can be used as a potential anticonvulsant agent for pathological hypersynchrony conditions, such as epilepsy.

DETAILED DESCRIPTION OF THE INVENTION

Figure 1:
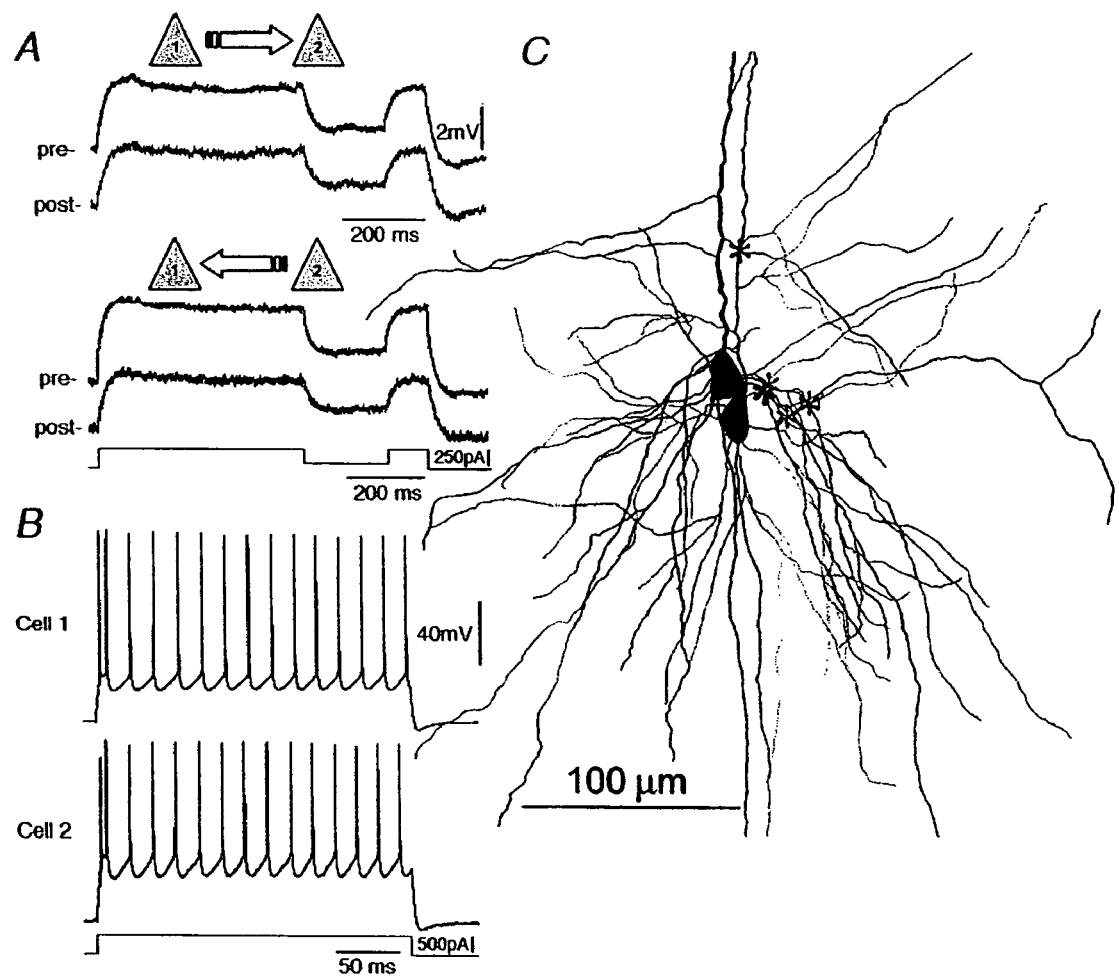
FIG. 1: A. Bi-directional responses to the sub-threshold depolarization and hyperpolarization recorded from a pair of electrically coupled pyramidal cells. B. Non-adapting firing patterns of the two pyramidal cells in A. C. The reconstruction of another electrically coupled pyramidal pair. Note that the somata are partially overlapped and the dendritic contacts are labeled with asterisks.

The present invention relates to a novel method for inhibiting signaling activity at pyramidal gap junctions. The method is based on the discovery that beta-amyloid, or peptides derived from beta-amyloid, have the ability to inhibit gap junction signaling in between pyramidal cells in an acute cortical slice preparation when such cells are contacted with a solution containing beta-amyloid.

Amyloids are made up of protein and polysaccharides. Beta-amyloid (Aβ) is a protein fragment of 39-43 amino acids and is the main constituent of amyloid plaques which are characteristing of various neurological disorders. Aβ circulates in human blood and in cerebrospinal fluid. Aβ peptides normally exist in human biological fluids and tissues at very low, nanomole, concentrations. They can also accumulate into plaques and are found in the brains of patients with Alzheimer's disease. Aβ1-40 is the predominant soluble species found in biological fluids. Typically, Aβ1-40 is present in the cerebrospinal fluid at a concentration of about 1 nM (Luo et al., *Brain Res.* 759, 287-95 (1997); Kontush et al., *Free Radic Biol Med.* 30, 119-28(2001); Plant, L. D., et al., *J Neurosci.* 23, 5531-5(2003); Kar, S., et al., *J Neurosci.* 16, 1034-40 (1996)). Aβ1-42 is also common but is normally found in even lower concentrations. Aβ1-42 is found in much larger proportions in senile plaques. Aβ25-35 is a commercially available fragment frequently used in research.

As discussed in the Exemplification section which follows, three species of Aβ were tested in the electrically coupled pairs of pyramid cells for their ability to inhibit gap junctional responses. The tested species were Aβ25-35, Aβ1-40 and Aβ1-42. As indicated, all three species were shown to consistently inhibit gap junctional responses within 10 minutes at low (100-200 nM) and at high (400 nM-1 μM) concentrations. Importantly, reversibility of the gap junctional inhibition was also demonstrated by peptide washout performed at various time points. With respect to all tested species, gap junctional activity was restored by a 10 minute washout. Under calcium-free conditions, the reported inhibition was observed at Aβ concentrations as low as 1 nM.

Thus, in one aspect, the present invention relates to a method for inhibiting gap junction-mediated signaling in pyramid cells by contacting the cells with Aβ, or a biologically active fragment thereof. As reported in the Exemplification section which follows, all of the Aβ peptides tested demonstrated the ability to inhibit gap junction-mediated signaling. One of these tested peptides, Aβ25-35, is substantially shorter than the other tested peptides and is comprised of only 11 amino acid residues. While not wishing to be bound by theory, this observation is consistent with the presence of an activity-enabling conformation encoded by the Aβ25-35 subdomain. This theoretical consideration notwithstanding, one of skill in the art would predict with a high degree of certainty based on the experiments reported herein that any Aβ peptide fragment, which contains at least residues 25-35, would exhibit the desired gap junctional signaling inhibition property.

As discussed in the Background of the Invention section, gap junction signaling inhibitors have been shown to have powerful anticonvulsant effects and have been used in the treatment of epilepsy. However, compounds currently known to possess this inhibitory activity are associated with undesirable side effects and can be unreliable. The use of a naturally occurring peptide such as Aβ, which is already present in the body at nanomolar concentrations, would not result in the toxic effects reported in connection with prior art gap junction signaling inhibitors.

The methods of the present invention would be practiced by the systemic administration of Aβ, or a biologically active fragment thereof. In preferred embodiments this would include intravenous, intramuscular, topical or subcutaneous delivery of a solution containing an effective amount of Aβ. Aβ1-40 is present at about 1 nM concentrations in the cerebrospinal fluid of normal individuals. To achieve a concentration of 1 nM in vivo, the patient would have to be treated with a dose higher than 1 nM. Therefore an effective dose should be at least 1 nM. However, individuals will vary in their baseline Aβ levels. In the situation where a patient is deficient in making Aβ any increase in Aβ levels may be therapeutic.

The effectiveness of Aβ is observable at various concentrations. Each of the three species tested is effective at inhibiting gap junction activity in electrically coupled pairs at low (100-200 nM) and at high (400 nM-1 μM) concentrations of Aβ. Aβ is also an effective inhibitor at concentrations even lower than 10 nM. As discussed in the Exemplification section which follows, this can be observed by stimulating pyramid cells extracellularly under calcium-free conditions. Calcium-free conditions shut down the chemical synaptic signals and, hence, isolate the gap junctional signals. Under such experimental conditions, concentrations of Aβ as low as 1 nM, which is the normal biological concentration, are effective at inhibiting electrical gap junctional signals.

One prevalent pathological hypersynchrony condition is epilepsy. The present invention includes the treatment of a patient, human or non-human animal, afflicted with epilepsy by administering an effective dose of Aβ. Furthermore, the invention includes administering Aβ as a treatment for any pathological hypersynchrony condition and is not limited to the treatment of epilepsy.

In the methods of the present invention, Aβ or a biologically active fragment(s) thereof may be administered to a human or non-human animal in a physiologically acceptable carrier in a therapeutically effective amount. A "biologically active fragment" thereof is intended to encompass any mimetic, truncation, deletion, and/or substitution of full-length Aβ with the ability to inhibit gap junction signaling in the methods of the present invention. Said compound or compounds may be administered alone or in combination with other therapies and may be delivered intravenously, subcutaneously, intramuscularly, topically, or orally to the human or non-human animal patient. There are techniques being developed which are useful for orally delivering active peptides. Progress has been made in the oral delivery of other peptide drugs, such as insulin. Aβ is a much shorter peptide than insulin and is probably easier to administer.

EXEMPLIFICATION

Several studies of synaptic transmission in the neocortex have been carried out and a research approach has been established for the study of single synaptic connections (Wang, Y. et al., *J Physiol* (London) 15, 65-90 (2004); Gupta, A. et al., *Science* 287, 273-8 (2000); Wang, Y., et al., *Cereb Cortex* 12, 395-410 (2002); Wang, Y. et al., *Nat Neurosci* 9(4), 534-42 (2006)). The same approach is useful in the study of pyramidal gap junctions and the effects of Aβ on these electrical synapses in the neocortex. These studies provide direct evidence for the existence of pyramidal gap junctions and reveal an inhibiting effect of Aβ on gap junctions in the neocortex.

Electrophysiological Recordings

Prefrontal or visual cortical slices (300 μm) were prepared from young (12-18 days) and adult (1-3 months) rats and young adult ferrets (6-9 weeks) by using a published protocol (Wang, Y. & Goldman-Rakic, P. S., *Proc Natl Acad Sci U S A* 101, 5093-8. Epub 2004 Mar 29. (2004)). Triple/quadruple patch clamp recordings were carried out to capture electrical synaptic connections formed between single pyramidal neurons in layer V of the medial prefrontal and visual cortical areas (Wang, Y. et al., *J Physiol* (London) 15, 65-90 (2004)). Neurons were filled with biocytin by diffusion during recordings, enabling selective staining of the recorded cells after recording.

In order to study the basic physiological properties of pyramidal gap junctions, multiple electrophysiological parameters were collected by recording electrically coupled pyramidal pairs. These parameters include: 1) sub-threshold responses to depolarizing and/or hyperpolarizing currents; 2) the step-coupling and spike-coupling coefficients, defined as the ratio between the membrane voltage changes of a post-junctional cell and a pre-junctional cell subjected to long weak stimulation (step) or brief strong stimulation (spike); 3) the co-firing rate defined as the percentage of the gap junctional responses occurring within 0.3 ms intervals between the two coupled neurons; 4) the reciprocity and symmetry of each pyramidal gap junction; 5) the amplitude of gap junctional responses; and 6) the synaptic plasticity of the gap junctional responses to the tetanus stimulations. Based on these parameters, further analysis for the gap junctional responses was carried out, including measurements of rising time, decay time, coupling time intervals, etc.

Evidence for Pyramidal Gap Junctions in the Neocortex

Direct demonstration of electrical coupling was made feasible by differential interference contrast infrared videomicroscopy (IR-DIC) and patch clamp recording from neighboring neurons under visual control (Bennett and Zukin, 2004). The gap junctions were directly recorded from two neighboring pyramidal neurons and verified by the responses of one cell to the sub-threshold depolarizing and hyperpolarizing pulses injected into the other cell (FIG. 1A). The responses were induced reciprocally from the two pyramidal cells that formed a gap junction. During recording, the neuronal firings were also recorded briefly by giving near threshold depolarization for the identification of electrophysiological types of the recorded neurons (FIG. 1B). Subsequently, the recorded cells were histochemically stained and 3D-computer reconstructed so that the neuronal anatomical types could be further identified and coupling sites could be labeled (FIG. 1C).

For the present invention, eight pairs of pyramidal gap junctions were obtained from the prefrontal cortex and visual cortex of ferrets and rats: four pairs from rat prefrontal cortex (14 to 28 postnatal days), three pairs from ferret prefrontal cortex (6, 7 and 9 weeks respectively), and one pair from ferret visual cortex (6 weeks).

Taking into consideration the low probability of obtaining a pair of electrically coupled pyramidal cells, gap junctional activity recorded from pyramidal cells was obtained and the effects of Aβ on the activity was observed under calcium-free conditions. Calcium-free conditions can shut down the chemical synaptic transmission and hence isolate the gap junctional activity, including responses induced by extracellular stimulations and spontaneous responses.

Treatments of Soluble Synthetic Aβ Peptides

To measure inhibition of gap junctional activity, three species of Aβ (Aβ25-35, Aβ1-40 and Aβ1-42) were tested in pairs of pyramid gap junctions. Treatments of soluble synthetic Aβ peptides at low (100~200 nM) and high (400 nM~1 μM) concentrations were prepared and bath-applied to the pyramidal gap junctions. The soluble peptides were prepared as 0.1 mM stock in 2.5% DMSO, 25 mM Tris, pH 7.4 and stocked at −80° C. Different concentrations of Aβ were freshly prepared by defrosting and diluting the stock solution with artificial cerebrospinal fluid before using. Each species was tested in three pairs of pyramidal gap junctions and at a low and a high concentration. Recordings of gap junctional responses were taken and compared for the gap junctional activity under Aβ treated and non-Aβ treated conditions. The pyramidal gap junctional activity was very sensitive to the soluble Aβ. All three species of Aβ consistently inhibited the gap junctional responses within 10 minutes.

Figure 2:
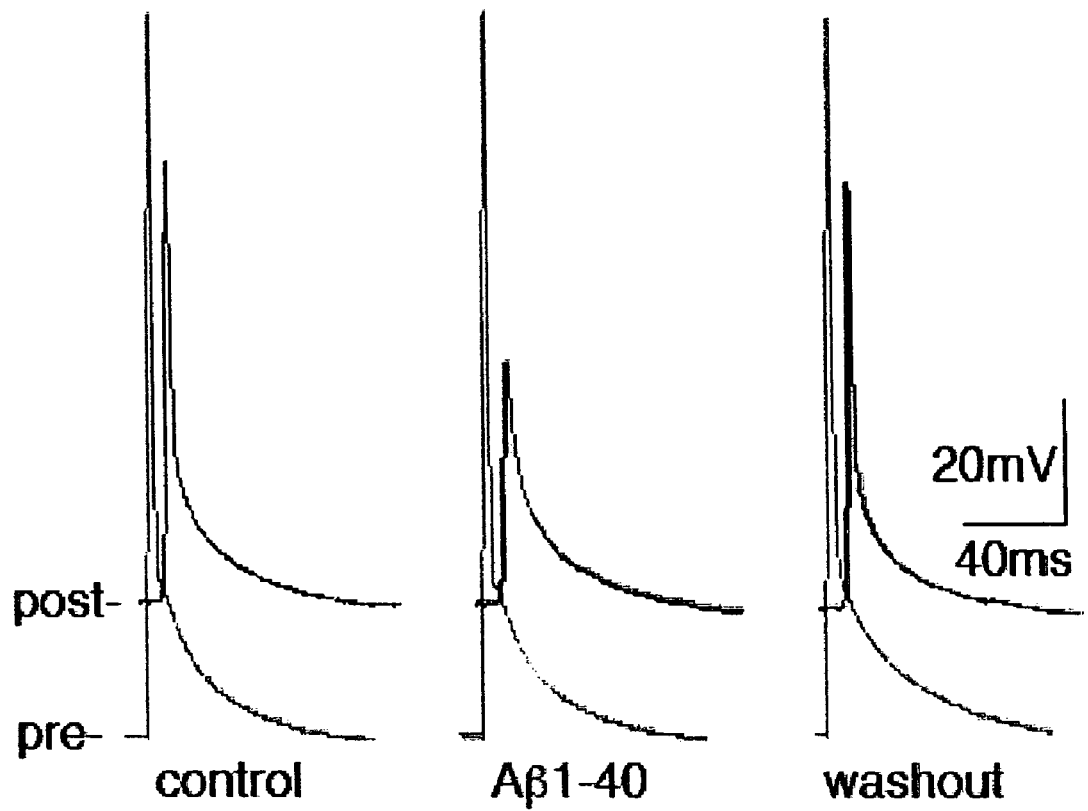
FIG. 2: Aβ inhibition of a pyramidal gap junction. The postjunctional responses (black traces) were reduced nearly 50% by bath-applying 1 μM Aβ1-40 for 10 minutes, and recovered by washout for 10 minutes. Presynaptic action potentials, which are not influenced by the application of Aβ1-40, are in grey.

Furthermore, to assess reversibility of the inhibition caused by Aβ washouts of the Aβ peptide were performed at various time points. The times for recovery back to a baseline reading were measured. In all three species, the inhibition responses were recovered by washout within 10 minutes (see FIG. 2).

The inhibition of the gap junctional responses between pyramidal cells was also recorded at Aβ concentrations lower than 10 nM (as low as 1 nM) by stimulating the cells extracellularly and recording the gap junctional responses under calcium-free conditions (n=9). Calcium-free conditions shut down the chemical transmission and hence isolate the gap junctional responses.

All data presented were based on the direct recordings of single gap junctions formed between pairs of pyramidal neurons and then confirmed anatomically by subsequent histochemical staining and 3D-computer reconstruction. The experimental results obtained from the electrically coupled pairs were consistent across many experiments, including those experiments performed at much lower concentrations of Aβ under calcium-free conditions.

Histochemical Staining

After recording, the slices were fixed for at least 24 h in a cold 0.1 M phosphate buffer (pH 7.4) containing 2% paraformaldehyde and 1% glutaraldehyde. Thereafter, the slices were rinsed and then transferred into a phosphate-buffered 3% $H_2O_2$ to block endogenous peroxidases. After rinsing in the phosphate buffer, slices were incubated overnight at 4° C. in an avidin-biotinylated horseradish peroxidase (ABC-Elite, Vector Labs; 2% A, 2% B and 1% Triton X-100). Subsequently, sections were rinsed again in the phosphate buffer and developed with diaminobenzidine under visual control using a bright-field microscope (Zeiss Axioskop) until all processes of the cells were clearly visible. Finally, the reaction was stopped by transferring the sections into the phosphate buffer. After rinsing in the phosphate buffer, slices were mounted in an aqueous mounting medium.

3D-computer Reconstruction

The well stained pyramidal pairs were reconstructed into 3D-computer model neurons using the Neurolucida system and a bright-field light microscope. Reconstructed neurons underwent quantitative analysis using the NeuroExplorer (MicroBrightField Inc, USA). Putative electrical synapses were identified according to the following criteria: (a) the same plane of focus (microscope lens with ×60 magnification, numerical aperture=0.9; resolution along the Z-axis=0.37 μm) is used, making sure the contacting structures (somatic or dendritic or axonal) have membranes within <0.5 μm of each other; (b) if the somatic or dendritic structure is thick (>2 μm), then a greater distance between the contacted membrane is allowed, providing that the somata are overlapped or touching each other, and the course of the dendrites or axonal collaterals are running parallel and touching or crossing each other.

Administering Aβ causes quick and reversible inhibition of pyramidal gap junction activity even at biological concentration levels. The three different species of Aβ peptides (e.g., Aβ 25-35, Aβ 1-40 and Aβ 1-42) are potentially useful as an anticonvulsant treatment. Aβ 25-35 shows the same effect as Aβ 1-40 and Aβ 1-42, indicating that even partial segments of the Aβ peptides may have an anticonvulsant effect. The side effects of Aβ should be minimal compared with other anticonvulsant chemical compounds due to Aβ's biological origin and low effective dose. Inhibition is quick and reversible even at biological concentration levels.

Although amyloid is considered to be a major causal factor of Alzheimer's disease, it should not be problematic when used as an anticonvulsant agent because: 1) the low effective concentrations of Aβ are near biological levels while Alzheimer's disease is related to Aβ accumulation and deposition; 2) most epilepsy subjects are young while Alzheimer's disease occurs at older ages possibly due to the dysfunction of metabolism of amyloid proteins.

Aβ Amino Acid Sequence Listing (SEQ ID NO: 1)
β-Amyloid [1-42](Aβ1-42)
H2N-DAEFRHDSGYEVHHQKLVFFAEDVGSNKGAIIGLMVGGVVIA-OH (SEQ ID NO: 2)
β-Amyloid [1-40](Aβ1-40)
H2N-DAEFRHDSGYEVHHQKLVFFAEDVGSNKGAIIGLMVGGV
V-OH (SEQ ID NO: 3)
β-Amyloid [25-35](Aβ25-35)
H2N-GSNKGAIIGLM-OH

What is claimed is:

1. A method for reducing or inhibiting gap junction-mediated signaling in pyramid cells comprising contacting said cells with beta-amyloid or a gap junction inhibiting fragment thereof and detecting the reduction or inhibition of gap junction-mediated signaling in pyramid cells.

2. A method of inhibiting gap junction-mediated signaling in pyramid cells comprising contacting said cells with a beta-amyloid peptide comprising amino acids 25-35 and detecting the reduction or inhibition of gap junction-mediated signaling in pyramid cells.

3. The method of claim 1 wherein the beta-amyloid is a peptide selected from the group consisting of: beta-amyloid 25-35, beta-amyloid 1-40, and beta-amyloid 1-42.

4. The method of claim 1 or claim 2 wherein the concentration of beta-amyloid is at least 1 nM.

5. A method of therapeutically treating a patient having symptoms of a pathological hypersynchrony condition comprising administering an effective dose of beta-amyloid, wherein said dose of beta-amyloid results in anti-convulsant effects in the patient.

6. The method of claim 5 wherein the patient is a human.

7. The method of claim 5 wherein the patient is a nonhuman animal.

8. The method of claim 5 wherein the condition is epilepsy.

9. The method of any one of claims 5-8, wherein the beta-amyloid is administered orally, subcutaneously, intramuscularly, topically or intravenously.

10. A method of reducing or inhibiting pyramidal cell gap junction activity in a subject, comprising administering to said subject an effective amount of a beta-amyloid peptide, such that pyramidal cell gap junction activity is inhibited, wherein said beta-amyloid peptide is of the formula SEQ ID NO: 1, SEQ ID NO: 2, or SEQ ID NO: 3 and wherein the reduction or inhibition of pyramidal cell gap junction activity is detected in the subject.

* * * * *